United States Patent [19]
Karami

[11] 3,948,267
[45] Apr. 6, 1976

[54] DIAPER WITH TAPE FASTENER

[75] Inventor: Hamzeh Karami, Crystal Lake, Ill.

[73] Assignee: Colgate-Palmolive Company, New York, N.Y.

[22] Filed: Feb. 24, 1975

[21] Appl. No.: 552,586

[52] U.S. Cl. .................. 128/287; 24/67 R; 128/284
[51] Int. Cl.² .................... A61F 13/16; A41B 13/02
[58] Field of Search ........... 128/284, 286, 287, 296; 24/67 R, 67 AR

[56] References Cited
UNITED STATES PATENTS

| | | | |
|---|---|---|---|
| 3,620,217 | 11/1971 | Gellert | 128/284 |
| 3,646,937 | 3/1972 | Gellert | 128/287 |
| 3,776,234 | 12/1973 | Hoey | 128/287 |
| 3,810,472 | 5/1974 | Aldinger et al. | 128/287 |
| 3,848,594 | 11/1974 | Buell | 128/284 |
| 3,875,621 | 4/1975 | Karami | 24/67 |

Primary Examiner—Aldrich F. Medbery
Attorney, Agent, or Firm—Powell L. Sprunger

[57] ABSTRACT

A tape fastener for a disposable diaper having opposed surfaces and opening means extending through the diaper. The tape fastener has a pressure-sensitive tape strip having a first portion secured to one surface of the diaper with adhesive on the first portion being exposed through the opening means. The fastener also has a release sheet having an adhesive bearing surface secured to the other surface of the diaper with adhesive exposed through the opening means. Adhesive on the first portion of the tape strip is attached to adhesive on the release sheet to anchor the tape strip to the release sheet.

18 Claims, 10 Drawing Figures

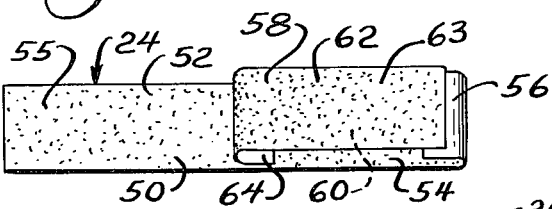
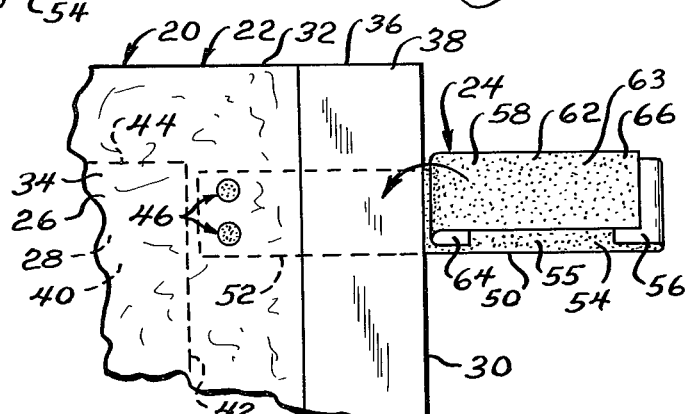
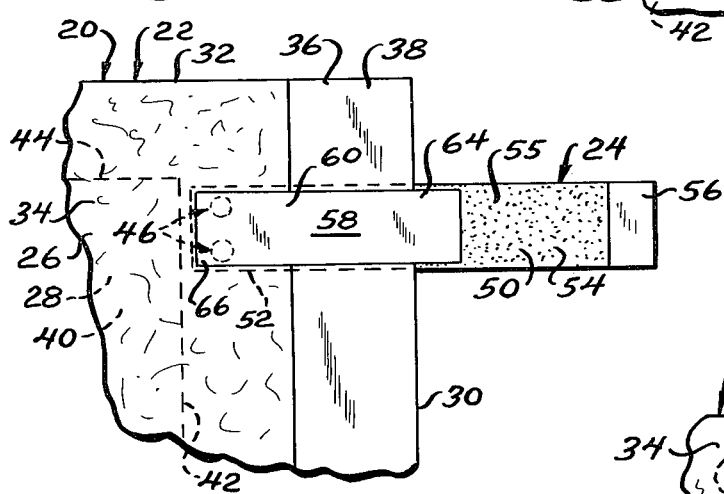
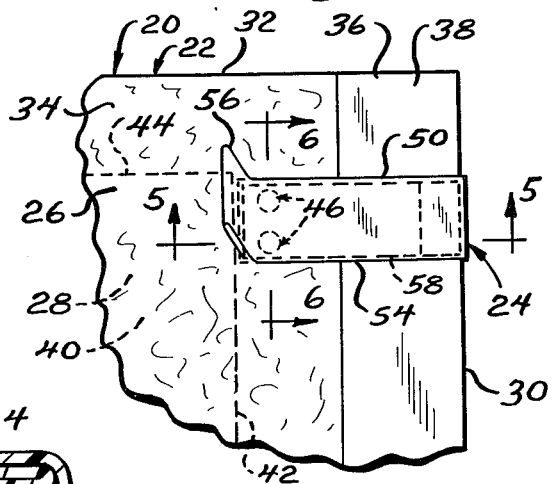
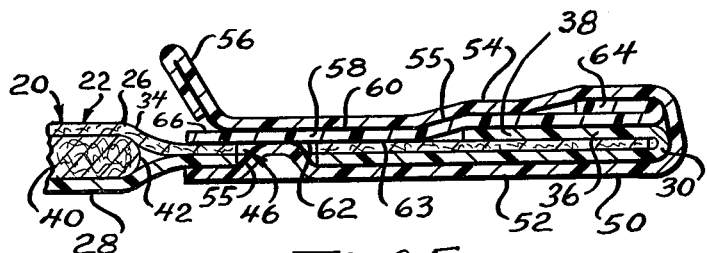

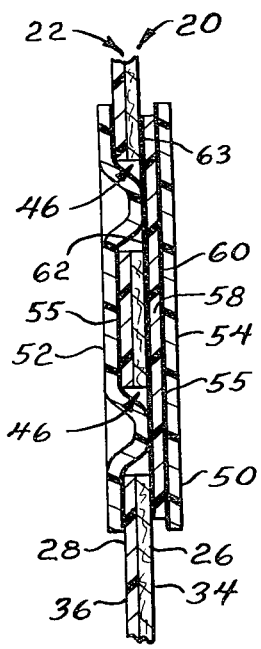
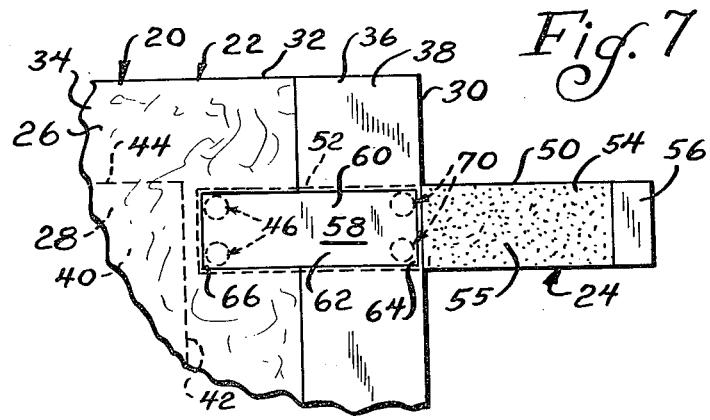
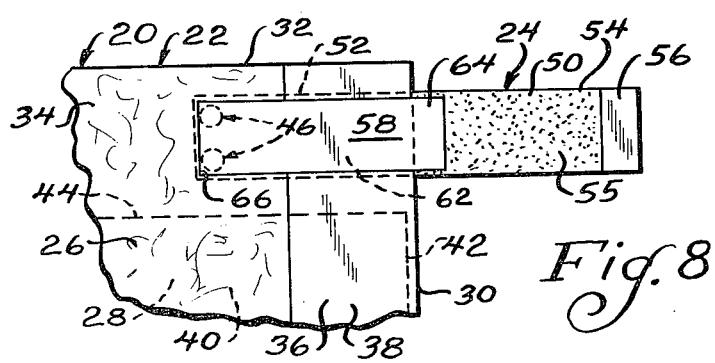
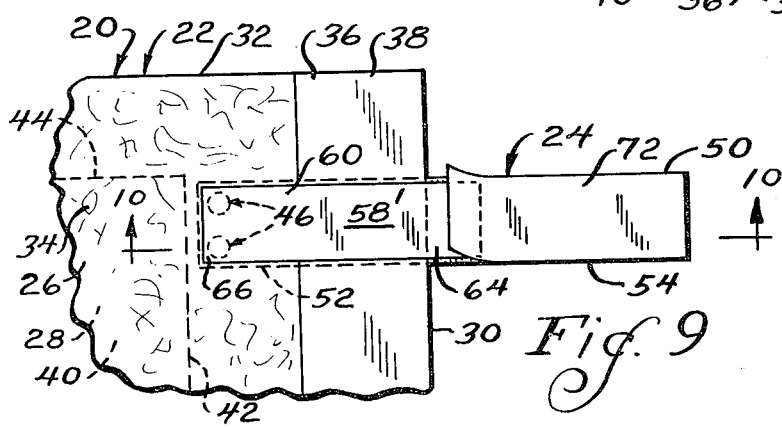
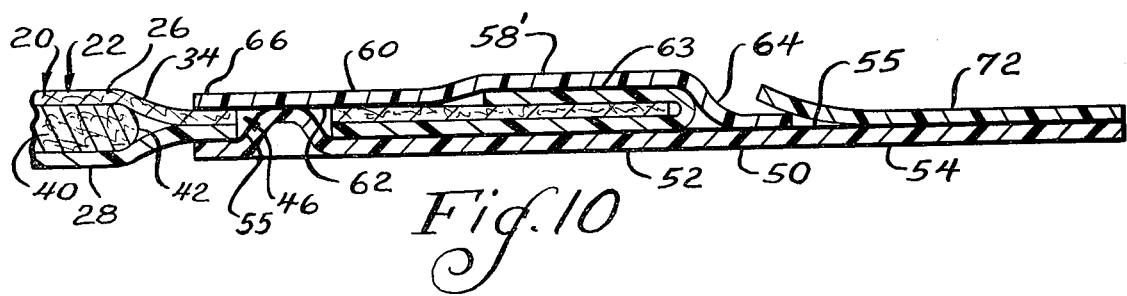

3,948,267

DIAPER WITH TAPE FASTENER

BACKGROUND OF THE INVENTION

The present invention relates to absorbent articles, and more particularly to disposable diapers.

A various assortment of disposable diapers have been proposed for use on infants. A number of such diapers have been provided with tape fasteners for securing the diaper about the infant during placement. The tape fasteners have generally taken the form of a tape strip having a securement portion which is covered by a release sheet, with the release sheet being removed from the securement portion of the tape strip during placement of the diaper to expose adhesive on the securement portion.

Since the diapers are disposable and thus discarded after a single use, it is desirable that the diapers be made of economic construction to reduce the cost to the consumer. Accordingly, it is desirable that the plastic backing sheet, which normally covers the back surface of the diaper, be made as thin as possible without detracting from the diaper's function as a cost saving measure. However, it has been found that the tape strips which are attached to the backing sheet tear out of the backing sheet during use of the diaper if made too thin, although such thin backing sheets would otherwise be suitable.

SUMMARY OF THE INVENTION

A principal feature of the present invention is the provision of a disposable diaper of simplified construction and reduced cost.

The diaper has an absorbent pad assembly having an absorbent pad, a fluid impervious backing sheet defining a back surface, a front surface, at least one side edge, and opening means extending through the pad assembly and spaced from the side edge. The tape fastener comprises, a pressure-sensitive tape strip having a first end section secured to the backing sheet with adhesive on the first end section being exposed through the opening means of the pad assembly, and a second securement end section extending past the side edge of the pad assembly. The tape fastener also has a sheet, such as a release sheet, having a first surface which may provide a relatively low affinity for adhesive on the tape strip and having a second adhesive-bearing surface secured to the front surface of the pad assembly. The adhesive of the tape strip exposed through the opening means contacts the adhesive on the second surface of the sheet adjacent one end and anchors the first end section of the tape strip to the sheet.

In one embodiment, the sheet extends from the opening means past the side edge of the pad assembly, with the second adhesive surface of the other end of the sheet being attached to adhesive on the second end section of the tape strip. In another embodiment, the pad assembly has second opening means adjacent the side edge of the pad assembly, with adhesive of the first end section of the tape strip being exposed through the second opening means. The adhesive on the strip exposed through the second opening means contacts adhesive on the other end of the sheet adjacent the side edge of the pad assembly, and anchors the strip to the other end of the sheet.

Thus, a feature of the present invention is that the sheet is permanently retained against the front surface of the pad assembly, and need not be discarded after placement of the diaper.

Another feature of the present invention is that the tape strip is anchored to the sheet by the adhesive on the strip and sheet.

A further feature of the invention is that anchorage of the strip to the sheet prevents the first end section of the strip from tearing out of the backing sheet during use of the diaper.

Further features will become more fully apparent in the following description of the embodiments of this invention and from the appended claims.

DESCRIPTION OF THE DRAWINGS

In the drawings:

FIG. 1 is a perspective view of a tape fastener according to the present invention prior to placement on a diaper;

FIG. 2 is a fragmentary plan view of a disposable diaper showing the tape fastener of FIG. 1 as partially applied to the diaper;

FIG. 3 is a fragmentary plan view of the diaper showing the tape fastener of FIG. 1 as secured to the diaper;

FIG. 4 is a fragmentary plan view of the diaper of FIG. 3 showing a securement portion of a tape strip releasably attached to a release sheet in the tape fastener;

FIG. 5 is a fragmentary sectional view taken substantially as indicated along the line 5—5 of FIG. 4;

FIG. 6 is a fragmentary sectional view taken substantially as indicated along the line 6—6 of FIG. 4;

FIG. 7 is a fragmentary plan view of a diaper showing another embodiment of the tape fastener of the present invention;

FIG. 8 is a fragmentary plan view of another embodiment of the tape fastener and diaper of the present invention;

FIG. 9 is a fragmentary plan view of a diaper showing another embodiment of the tape fastener of the present invention; and FIG. 10 is a fragmentary sectional view taken substantially as indicated along the line 10—10 of FIG. 9.

DESCRIPTION OF THE PREFERRED EMBODIMENTS

Referring now to FIGS. 4 and 5, there is shown a disposable diaper generally designated 20 having an absorbent pad assembly 22 and a tape fastener 24 secured to the pad assembly 22. The pad assembly 22 has a front surface 26, a back surface 28, a side edge 30, and an end edge 32 connecting the side edge 30. The pad assembly 22 has a fluid pervious cover sheet 34 defining a substantial portion of the front surface 26 of the pad assembly, a fluid impervious backing sheet 36, such as polyethylene, defining the back surface 28 of the pad assembly and having a lateral side margin 38 folded over and secured to the front surface 26 of the pad assembly, and an absorbent pad 40 intermediate the cover and backing sheets 34 and 36. The backing sheet 36 may have a reduced thickness on the order of 0.3 to 0.9 mils to reduce the cost of the backing sheet and diaper. The absorbent pad 40 has a side edge 42 spaced from the side edge 30 of the pad assembly 22, and an end edge 44 connecting the side edge 42 and spaced from the end edge 32 of the pad assembly 22. As shown in FIGS. 2–6, the pad assembly 22 also has opening means 46 extending through the pad assembly, and spaced from the side edge 30 of the pad assembly 22. In this embodiment, the opening means 46 comprises a pair of spaced openings which are located intermediate the side edge 42 of the absorbent pad and the side edge 30 of the pad assembly. The openings are spaced longitudinally relative the diaper and laterally across an underlying tape strip, as will be seen below. It is understood that the opposed side of the diaper (not shown) would normally have a structure substantially similar to that described above, and would include a tape fastener as described below.

As shown in FIG. 1, the tape fastener 24 has an elongated pressure-sensitive tape strip 50 having a first end section 52, a second securement end section 54, and adhesive 55 on one surface of the strip. The tape strip 50 may have a folded over end 56 adjacent the outer end of the second end section 54 defining tab means for a purpose which will be described below. The tape fastener 24 also has a release sheet 58 having a first surface 60 providing a relatively low affinity for the adhesive 55 on the tape strip 50, and a second opposed surface 62 having a coating of adhesive 63. The adhesive 63 on one end 64 of the release sheet 58 is attached to the adhesive 55 on the second end section 54 of the tape strip 50, in order to retain the one end 64 to the tape strip, as described below. The first surface 60 of the release sheet 58 may be treated to obtain the desired affinity for the adhesive 55. For example, the first surface of a paper strip, serving as the release sheet, may be treated with a silicon release coating to obtain the desired release characteristics from the adhesive.

As shown in FIG. 2, the first end section 52 of the tape strip 50 is secured to the backing sheet 36, such that adhesive on the first end section 52 is exposed through the openings or opening means 46. As illustrated in FIG. 2 and 3, the other end 66 of the release sheet 58 is folded over the front surface 26 of the pad assembly 22, with the adhesive 63 on the release sheet 58 attached to the front surface 26 of the pad assembly, and with a portion of the adhesive 63 on the release sheet exposed through the opening means 46. Since the side edge 42 of the absorbent pad 40 is spaced from the opening means 46, the relatively thin cover and backing sheets 34 and 36 present only a slight spacing between the other end 66 of the release sheet 58 and the first end section 52 of the tape strip 50. The other end 66 of the release sheet 58 may be pressed against the pad assembly, in order that the adhesive 55 and 63, which is exposed through the opening means 46, is placed into contact. Accordingly, the second section 54 of the tape strip is anchored to the one end 64 of the release sheet by the adhesive 55 and 63, while the first end section 52 of the tape strip is firmly anchored to the release sheet by the adhesive 55 and 63 in contact through the opening means 46. The release sheet thus prevents the first end section 52 of the tape strip from tearing out of the relatively thin backing sheet during use of the diaper.

As shown in FIGS. 3–6, the second end section 54 of the tape strip 50, including the one end 64 of the release sheet 58, is folded over the front of the diaper and the second end section 54 of the tape strip 50 is releasably attached to the first surface 60 of the release sheet 58. Since the first surface 60 of the release sheet 58 has a relatively low affinity for the adhesive on the second end section 54 of the tape strip, the second end section of the tape strip may be readily removed from the release sheet 58 during placement of the diaper. Removal of the second end section 54 from the release sheet 58 is facilitated by the tab 56 at the outer end of the second end section, which is free of attachment to the release sheet 58 or the pad assembly 22. After the second end section 54 of the tape strip 50 is removed from the first surface 60 of the release sheet 58, in the position as shown in FIG. 3, the second end section 54 is properly located for securing the diaper 20 about the infant. Thus, securement of the diaper is accomplished without removal of the release sheet from the pad assembly, eliminating the necessity for separately discarding release sheets after placement of the diaper.

Another embodiment of the present invention is illustrated in FIG. 7, in which like reference numerals designate like parts. In this embodiment, the side edge 42 of the absorbent pad 40 is spaced from the side edge 30 of the pad assembly 22, and the opening means 46 is located intermediate the side edge 42 of the absorbent pad and the side edge 30 of the pad assembly, as previously described. However, in this embodiment, the pad assembly has second opening means 70 extending through the pad assembly and located adjacent the side edge 30 of the pad assembly, with adhesive on the first end section 52 of the tape strip 50 also being exposed through the second opening means 70. In this embodiment, the one end 64 of the release sheet 58 is located adjacent the side edge 30 of the pad assembly 22 with adhesive on the release sheet being exposed through the second opening means 70. Thus, the adhesive of the strip 50 exposed through the second opening means 70 contacts the adhesive on the one release sheet end 64, and anchors the tape strip to the one end 64 of the release sheet 58, while the adhesive on the strip exposed through the first opening means 46 anchors the strip 50 to the adhesive on the other end 66 of the release sheet, as previously described. Accordingly, the first section 52 of the tape strip is anchored to both ends of the release sheet to prevent the tape strip from tearing out of the backing sheet.

Another embodiment of the tape fastener of the present invention is illustrated in FIG. 8, in which like reference numerals designate like parts. In this embodiment, the side edge 42 of the absorbent pad 40 extends to a location adjacent the side edge 30 of the pad assembly 22. Since the bulk of the absorbent pad 40 may make it difficult to secure the first end section 52 of the tape strip to the release sheet 58 through opening means which extends through the pad 40 itself, in this embodiment the tape fastener 24 is located intermediate the end edge 44 of the absorbent pad 40 and the end edge 32 of the pad assembly 22. In this region, the relatively thin thickness of the cover and backing sheets 34 and 36 does not impair attachment of the adhesive on the first end section 52 to the adhesive on the release sheet. In other respects, the tape fastener 24 of FIG. 8 is similar to that described in connection with FIGS. 1–6.

Another embodiment of the present invention is illustrated in FIGS. 9 and 10, in which like reference numerals designate like parts. In this embodiment, a release sheet 72 is releasably attached to the adhesive on the second end section 54 of the tape strip 50. The release sheet 72 is removed from the second end section 54 during placement of the diaper to expose the underlying adhesive which is then used to secure the diaper about the infant. In this embodiment, the sheet 58', which need not have a treated first surface 60, serves to obtain improved anchorage of the first end section 52 of the tape strip 50 to the diaper, as previously described. The first end section 52 of the tape strip is attached to adhesive 63 on the release sheet 58 through the opening means 46 and at the one end 64 of the sheet 58', thus preventing the first end section 52 of the tape strip 50 from being torn from the back sheet and being pulled away from the diaper.

The foregoing detailed description is given for clearness of understanding only, and no unnecessary limitations should be understood therefrom, as modifications will be obvious to those skilled in the art.

I claim:

1. A disposable diaper, comprising:
   an absorbent pad assembly having an absorbent pad, a fluid impervious backing sheet defining a first surface of the diaper, a second opposed surface, at least one side edge, and opening means extending through the pad assembly and spaced from said side edge; and
   a tape fastener comprising,
     a pressure-sensitive tape strip having a first end section secured to said backing sheet with adhesive on the first end section being exposed through said opening means of the pad assembly, and a second securement section extending past said side edge of the pad assembly, and
     a sheet having a first surface and a second adhesive-bearing surface secured to the second surface of the pad assembly, with said adhesive of the tape strip exposed through the opening means contacting the adhesive on the second surface of the sheet to anchor the first end section of the tape strip to said sheet.

2. The diaper of claim 1 wherein said first surface of said sheet has a relatively low affinity for adhesive on the tape strip, and the second section of the tape strip is releasably attached to the first surface of the sheet.

3. The diaper of claim 2 wherein said second section of the tape strip has tab means adjacent its outer end to facilitate removal of the second section from the sheet.

4. The diaper of claim 1 wherein said sheet extends from said opening means toward the side edge of the pad assembly.

5. The diaper of claim 4 wherein said sheet has one end extending past the side edge of the pad assembly, with adhesive on said one end of the sheet being attached to adhesive on the second section of the tape strip adjacent said side edge.

6. The diaper of claim 4 wherein said pad assembly includes aperture means intermediate said opening means and the side edge of the pad assembly, with adhesive on the first end section of the tape strip being exposed through said aperture means and contacting adhesive on the second surface of the sheet to anchor the first end section of the tape strip and said sheet together.

7. The diaper of claim 6 wherein one end of said sheet is located intermediate the aperture means and the side edge of the pad assembly.

8. The diaper of claim 6 wherein said aperture means is located adjacent the side edge of the pad assembly.

9. The diaper of claim 1 wherein an end edge of the sheet is located adjacent said opening means and remote the opening means relative the side edge of the pad assembly.

10. The diaper of claim 1 wherein said backing sheet has a thickness in the range of 0.3 to 0.9 mils.

11. The diaper of claim 1 wherein said absorbent pad includes at least one side edge spaced from the side edge of the pad assembly, and in which said opening means is located intermediate the side edge of the pad and the side edge of the pad assembly.

12. The diaper of claim 1 wherein said absorbent pad has an end edge spaced from an end edge of the pad assembly, and in which said tape fastener is located intermediate the end edge of the absorbent pad and the end edge of the pad assembly.

13. The diaper of claim 12 wherein the absorbent pad has a side edge located adjacent the side edge of the pad assembly.

14. The diaper of claim 1 wherein said opening means comprises a pair of spaced openings spaced laterally across the first end section of the tape strip.

15. The diaper of claim 1 including a release sheet releasably attached to the adhesive on the second section of the tape strip.

16. A disposable diaper, comprising:
    an absorbent pad assembly having a back surface, a front surface, at least one side edge, and opening means extending through the pad assembly, said opening means being spaced from the side edge of the pad assembly; and
    a tape fastener comprising,
      a pressure-sensitive tape strip having a first end section secured to the back surface of the pad assembly with adhesive on the first end section being exposed through said opening means of the pad assembly, and a second securement end section extending past the side edge of the pad assembly, and
      a release sheet having a first surface providing a relatively low affinity for adhesive on said tape strip and a second adhesive-bearing surface secured to the front surface of the pad assembly, with said adhesive exposed through the opening means on the tape strip contacting adhesive on the second surface of the release sheet adjacent one end of the release sheet, said release sheet extending past the side edge of the pad assembly with adhesive on the second surface of the other end of the release sheet being attached to adhesive on the second end section of the tape strip adjacent the side edge of the pad assembly to anchor the tape strip to the release sheet, said second end section of the tape strip being folded over and releasably attached to the first surface of the release sheet.

17. A disposable diaper, comprising:
    an absorbent pad assembly having a back surface, a front surface, at least one side edge, first opening means extending through the pad assembly and being spaced from the side edge of the pad assembly, and second opening means extending through the pad assembly and being located adjacent the side edge of the pad assembly; and
    a tape fastener comprising,
      a pressure-sensitive tape strip having a first end section secured to the back surface of the pad assembly with adhesive on the first end section being exposed through the first and second opening means of the pad assembly, and a second securement end section extending past the side edge of the pad assembly, and
      a release sheet having a first surface providing a relatively low affinity for adhesive on said tape strip and a second adhesive-bearing surface secured to the front surface of the pad assembly, with said adhesive exposed through the first and second opening means on the tape strip contacting the adhesive on the second surface of the release sheet to anchor the first end section of the tape strip to the release sheet, said second end section of the tape strip being folded over and releasably attached to the first surface of the release sheet.

18. A tape fastener for a disposable diaper having opposed surfaces and opening means extending through the diaper, comprising:

a pressure-sensitive tape strip having a first portion secured to one of the surfaces of the diaper with adhesive on the first portion being exposed through the opening means; and a release sheet having an adhesive bearing surface secured to the other surface of the diaper with adhesive exposed through the opening means, and with adhesive on the first portion of the tape strip being attached to adhesive on the release sheet through the opening means to anchor the tape strip to the release sheet.

* * * * *